United States Patent
Commereuc et al.

(10) Patent No.: US 6,437,209 B1
(45) Date of Patent: *Aug. 20, 2002

(54) PROCESS FOR METATHESIS OF OLEFINS IN THE PRESENCE OF A STABILIZING AGENT OF THE CATALYST

(75) Inventors: Dominique Commereuc, Meudon; Paul Mikitenko, Noisy le Roi, both of (FR)

(73) Assignee: Institut Francais du Petrole, Rueil Malmaison Cedex (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/493,255

(22) Filed: Jan. 28, 2000

(30) Foreign Application Priority Data

Jan. 29, 1999 (FR) .............................. 99 01277

(51) Int. Cl.[7] .............................. C07C 6/00; C07C 6/04
(52) U.S. Cl. ........................ 585/645; 585/643; 585/646; 585/647
(58) Field of Search ............................... 585/643, 645, 585/646, 647

(56) References Cited

U.S. PATENT DOCUMENTS

| | | | | |
|---|---|---|---|---|
| 4,709,115 A | * | 11/1987 | Jung et al. | 585/643 |
| 5,120,894 A | * | 6/1992 | McCauley | 585/664 |
| 5,218,131 A | * | 6/1993 | Warwel et al. | 554/163 |
| 5,596,115 A | * | 1/1997 | Commereuc | 556/27 |

FOREIGN PATENT DOCUMENTS

| | | | |
|---|---|---|---|
| EP | 0691318 A1 | * | 1/1996 |
| EP | 769323 | * | 4/1997 |

* cited by examiner

Primary Examiner—Thuan D. Dang
(74) Attorney, Agent, or Firm—Millen, White, Zelano & Branigan, P.C.

(57) ABSTRACT

Catalytic process for metathesis of olefins in the presence of a catalyst and a stabilizing agent that is injected into the reaction medium. Application in particular to rebalancing between one another the light olefins that are obtained from steam cracking or catalytic cracking (FCC), such as ethylene, propylene, butenes or pentenes.

17 Claims, 2 Drawing Sheets

Figure 1:
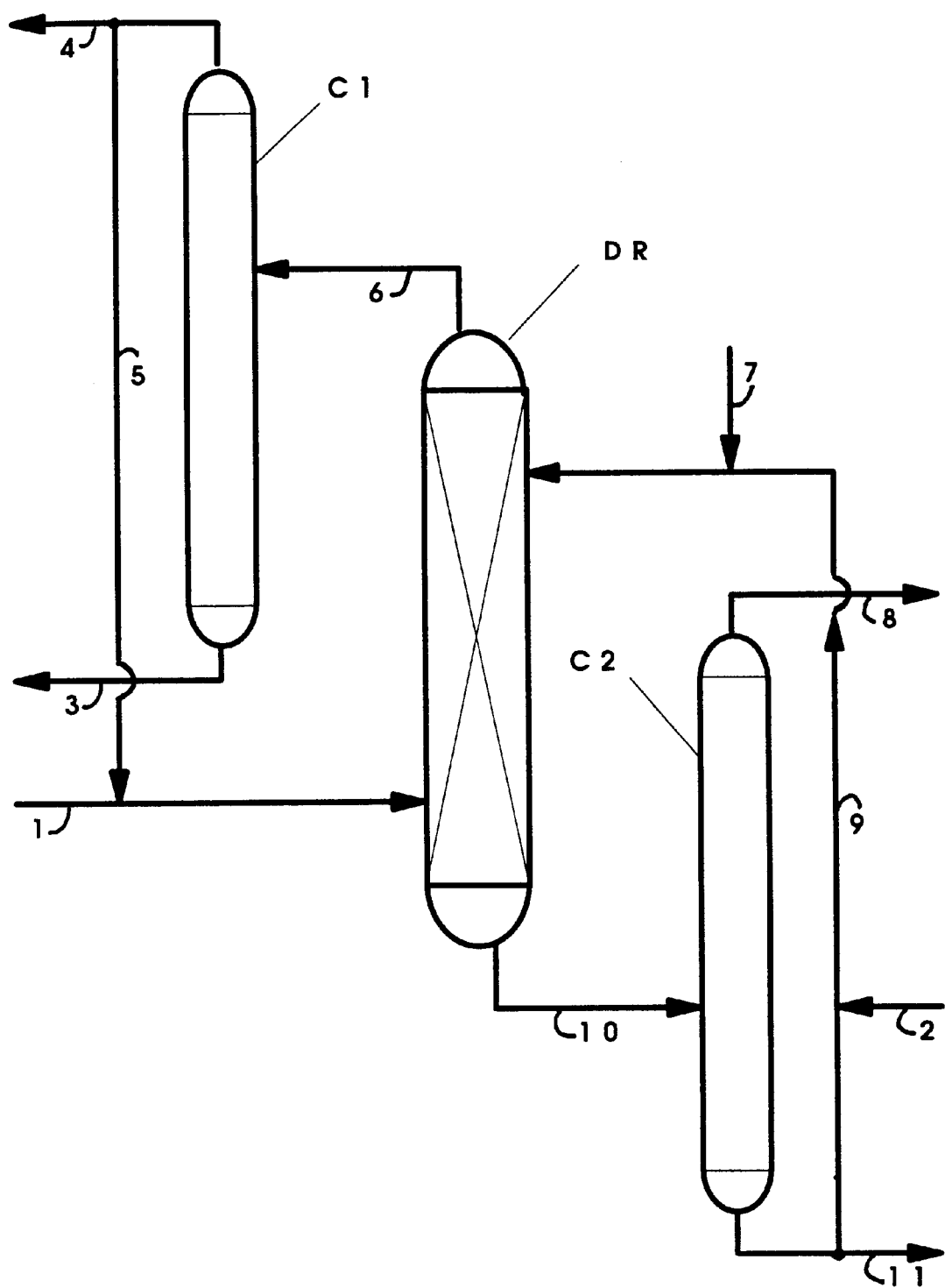

PROCESS FOR METATHESIS OF OLEFINS IN THE PRESENCE OF A STABILIZING AGENT OF THE CATALYST

This invention relates to a catalytic process for metathesis of olefins in the presence of a stabilizing agent that makes it possible to reduce the deactivation of the catalyst. The invention applies very advantageously when the reaction is carried out in a distillation column that comprises at least one catalytic reactive zone, called reactive distillation column below.

The metathesis of the olefins is a balanced reaction that consists of a statistical redistribution of the alkylidene groups of olefins that are brought together. They have a great deal of practical interest, for example for the rebalancing between one another of the light olefins that are obtained from steam cracking or catalytic cracking (FCC) or optionally a Fischer-Tropsch reaction, such as ethylene, propylene, butenes or pentenes. In a general way, it is catalyzed by the compounds of tungsten, molybdenum or rhenium. Due to its statistical nature, the reaction provides as a product a generally complex mixture that must be fractionated to be able to recycle unconverted reagents in the reactor so as to increase their conversion rate.

The metathesis reaction is usually carried out either in batch mode or continuously by using a reactor in which the catalyst is in the form of a fixed bed, a stirred bed, a fluid bed or a fluidized bed. At the end of the reaction (by batch) or at the outlet of the reactor (continuously), the effluent is directed toward the distillation columns to separate the products and the untransformed reagents. The diagrams of the metathesis processes are therefore generally complex due to the balanced nature of the reaction.

The use of a reactive distillation column in which the metathesis reaction and the separation of the reagents and products is done simultaneously can then in principle have numerous advantages, as is described in U.S. Pat. No. 4,709,115 for the dismutation of butene-1. In this case, the separation in situ, on the one hand of the reagents and products, and on the other hand of products between one another, makes it possible to increase significantly the conversion of the reagents and also the selectivity of the reaction by reducing the possibilities of secondary reactions of the products between one another. The possibility of use of a reactive metathesis distillation is also mentioned in Patent EP 832 867.

It was noted, however, that the metathesis catalysts, whether they are based on tungsten, molybdenum or rhenium, deactivate quickly over time and therefore require frequent regenerations. The regeneration method differs slightly depending on the metal and nearly always comprises at least one calcination phase of the catalyst at high temperature, for example between 400 and 1000° C. This does not pose any particular problem for implementation when the catalyst is placed in a fixed bed in a reactor that is designed accordingly or else transferred from the reactor into a regenerator thanks to a fluid bed or a fluidized bed. In contrast, the frequency of the regenerations considerably reduces the productivity of the installation.

On the contrary, the necessary implementation of frequent regenerations is a virtually insoluble problem if the catalyst is placed inside a distillation column that comprises plates or packing that are intended to promote the liquid-vapor contact. The technology of the reactive distillation thus cannot be applied at the industrial level with the conventional metathesis catalysts.

It has now been found, unexpectedly, that injection continuously, separately or with the metathesis feedstock of an aluminum compound $X_q AlR'_r$ makes it possible to reduce considerably the deactivation of the catalyst. Thus, it is possible to consider the implementation of the metathesis either in a conventional reactor with much more spaced regenerations or in a reactive distillation column.

The invention therefore relates specifically to a process for olefin metathesis in the presence of a catalyst or a stabilizing agent that is injected into the reaction medium. This means that the stabilizing agent is injected during the entire course of the metathesis process, whereby the injection takes place continuously or discontinuously.

An object of the invention is more specifically a process for metathesis of olefins, in which an aluminum compound $X_q AlR'_r$—in which X is a radical that is selected from the group that is formed by alkoxides and aryloxides RO—, sulfides RS— and amides $R_2N$—; R is a hydrocarbyl radical that contains 1 to 40 carbon atoms; R' is an alkyl radical that contains 1 to 20 carbon atoms; q and r are equal to 1 or 2 so that the sum of q+r is equal to 3—is injected into the reaction medium.

The stabilizing aluminum compound corresponds to general formula $X_q AlR'_r$. In this formula, X is a radical that is selected from the group that is formed by alkoxides and aryloxides RO—, sulfides RS— and amides $R_2N$—, R is a hydrocarbyl radical that contains 1 to 40 carbon atoms, for example, alkyl, cycloalkyl, alkenyl, aryl, substituted aryl or cycloalkyl, preferably a hydrocarbyl radical of 2 to 30 carbon atoms, whereby this radical can be substituted by at least one alkoxy group or at least one halogen. As an example, and without the list being limiting, R can be an ethyl, n-propyl, isopropyl, n-butyl, t-butyl, cyclohexyl, benzyl, diphenylmethyl, phenyl, methyl-2-phenyl, methyl-4-phenyl, methoxy-2-phenyl, methoxy-4-phenyl, dimethyl-2,6-phenyl, diisopropyl-2,6-phenyl, t-butyl-2-phenyl, t-butyl-2-methyl-4-phenyl, di-t-butyl-2,6-phenyl, di-t-butyl-2,6-methyl-4-phenyl, tri-t-butyl-2,4,6-phenyl, phenyl-2-phenyl, diphenyl-2,6-phenyl, fluoro-2-phenyl, fluoro-4-phenyl, pentafluorophenyl radical. In amides $R_2N$—, $R_2$ can constitute with nitrogen a nitrogenous heterocycle, such as pyrrolidine or piperidine. R' is an alkyl radical that contains 1 to 20 carbon atoms, preferably 1 to 6 carbon atoms, for example, methyl, ethyl, isobutyl, and q and r are equal to 1 or 2 so that the sum of q+r is equal to 3.

As preferred aluminum compounds, those will be cited that correspond to general formula $(RO)_q AlR'_r$, in which R is a hydrocarbyl radical that is selected from the group that is formed by the alkyl, cycloalkyl, alkenyl, aryl, substituted aryl or cycloalkyl radicals, a hydrocarbyl radical of 2 to 30 carbon atoms, whereby this radical can be substituted by at least one alkoxy group or at least one halogen, whereby the aryl and substituted aryl radicals are preferred. R' is selected from the group that is formed by the methyl, ethyl, isobutyl radicals, whereby the radicals contain 1 to 20 carbon atoms and whereby the radicals contain 1 to 6 carbon atoms.

The more particularly preferred aluminum compounds are selected from the group that is formed by bis-(di-t-butyl-2,6-methyl-4-phenoxy)-isobutyl-aluminum, bis-(di-t-butyl-2,6-methyl-4-phenoxy)-ethyl-aluminum, bis-(di-t-butyl-2,6-methyl-4-phenoxy)-methyl-aluminum.

The preparation of the $X_q AlR'_r$ is known in the literature. Any process for preparation of these compounds is suitable. In the case of compounds $(RO)_q AlR'_r$ (case where X=RO—), it is possible, for example, to react an alcohol or an ROH phenol with an $AlR'_3$ trialkylaluminum in an organic solvent, for example a hydrocarbon or an ether.

The injected stabilizing agent therefore plays the role of anti-deactivating agent, i.e., it reduces the deactivation of the catalyst and therefore makes it possible to increase the cycle length between two regenerations of the catalyst, thus considerably reducing the frequency of these regenerations.

The invention pertains to any metathesis catalyst, for example, the catalysts that are used conventionally and that comprise at least one element that is selected from among rhenium, molybdenum and tungsten, whereby rhenium is preferred. Among the conventional catalysts that contain rhenium, it is possible to cite the catalysts that are described in U.S. Pat. Nos. 4,795,734 and 5,449,852.

Metathesis catalysts with a rhenium base that are much more active than the conventional catalysts have been described in Patent EP 769 323. They comprise at least three components: a porous mineral substrate, 0.01 to 20% by weight of rhenium in oxide form, and 0.01 to 10% by weight of aluminum that is introduced in the form of a promoter aluminum compound of general formula $(RO)_q AlR'_r$, in which R is a hydrocarbyl radical that contains 1 to 40 carbon atoms, R' is an alkyl radical that contains 1 to 20 carbon atoms, q and r are equal to 1 or 2 such that the sum of q+r is equal to 3, whereby a heat treatment follows the impregnation.

In the case of these unconventional metathesis catalysts with a rhenium base, the aluminum compound of general formula $(RO)_q AlR'_r$ is therefore used both as a catalyst promoter during its preparation and then injected, preferably continuously, as a stabilizing agent of this catalyst.

The description of the preferred catalyst is restated below as in Patent EP 769 323.

The porous mineral substrate is advantageously a substrate with an acidic or neutral nature, more particularly an alumina, a silica or a silica-alumina that has a specific surface area of 10 to 400 $m^2/g$. The porous substrate preferably consists of alumina or a compound that contains at least 75% by weight of alumina, which is advantageously to have an appreciable surface area, for example at least 10 $m^2/g$, and preferably at least 50 $m^2/g$, an adequate pore volume, for example at least 0.1 ml/g and preferably 0.3–1 ml/g. It is possible to use, for example, an alumina of the same type as those of the catalytic reforming catalysts.

The precursor of the rhenium compound that is used is preferably selected from the group that is formed by rhenium heptoxide, ammonium perrhenate and perrhenic acid. The rhenium compound can be introduced onto the substrate by, for example, sublimation in vapor phase or by impregnation in solution. It is generally preferred to use the method of dry impregnation, where the rhenium compound is put into solution in the water or in an organic solvent, for example a hydrocarbon, an alcohol or an ether. The amount of rhenium on the substrate is regulated by the selection of the concentration of the impregnation solution, whereby its amount is such that the volume of this solution is equal to or slightly less than the pore volume of the solid that is to be impregnated. When the amount of rhenium that it is desired to impregnate is greater than that that makes it possible to introduce a solution at its saturation limit, the operation should be carried out several times with intermediate drying to eliminate the impregnation solvent at a temperature of, for example, 90 to 250° C., preferably 100 to 180° C. This makes it possible to introduce 0.01 to 20%, preferably 0.1 to 15% and even more advantageously 0.5 to 8% by weight of rhenium (expressed in metal rhenium).

After the rhenium precursor is introduced onto the substrate, drying is carried out at a temperature of, for example, 90 to 250° C., preferably 100 to 180° C., then a calcination at a temperature of, for example, 250 to 1000° C., and preferably 300 to 600° C., for a duration of 10 minutes to 10 hours, and preferably 30 minutes to 5 hours. After calcination, the solid is cooled under a dry and inert atmosphere, for example, under nitrogen or under argon.

Promoter aluminum compound $(RO)_q AlR'_r$ can be introduced onto the substrate by any methods that are known to one skilled in the art, but it is imperative to operate protected from air and moisture. It is possible to impregnate the substrate by excess solution that contains the aluminum compound. After a contact time which can range from several minutes to several days, the solid is drained and washed with solvent to eliminate the portion of the compound which is not attached. It is also possible, in an operating procedure that is preferred, to use the dry impregnation method. The concentration of aluminum of the solution is then adjusted based on the amount of aluminum that it is desired to deposit on the solid, so that the volume of this solution is equal to or slightly less than the pore volume of the solid that is to be impregnated. The solvent that is used in this impregnation is preferably an organic solvent, for example a hydrocarbon or an ether. This makes it possible to introduce 0.01 to 10%, preferably 0.05 to 5% and even more advantageously 0.1 to 5% by weight of aluminum (expressed in terms of metal aluminum).

After the compound of the promoter aluminum is introduced, the preparation of the catalyst can end with drying, under vacuum or under a gas stream that is preferably inert, at a temperature of 0 to 1000° C., preferably at a temperature that is close to ambient temperature, 0 to 50° C. No activation operation, chemical or thermal, is necessary to trigger the activity of these catalysts, and calcination is not recommended. It is sufficient to bring them into contact with an olefin so that the metathesis reaction starts.

Instead of preparing the compound $(RO)_q AlR'_r$ and bringing it into contact with the catalyst that is supported with rhenium, as described above, it is possible to put said catalyst that is supported with rhenium directly into contact with the precursors of compound $(RO)_q AlR'_r$, which are, for example, ROH and $AlR'_3$. In the same way as above, the preparation can end with drying.

In the metathesis process, the olefins that are able to react are monoolefins that have 2 to 30 carbon atoms, for example, ethylene, propylene, butenes, pentenes, hexenes, octenes, cycloolefins that have 3 to 20 carbon atoms, for example cyclopentene, cyclooctene, norbornene, polyolefins that have 4 to 30 carbon atoms, for example hexadiene-1,4, octadiene-1,7, cyclopolyolefins that have 5 to 30 carbon atoms, for example, cyclooctadiene-1,5, norbornadiene, dicyclopentadiene.

Other olefins that can react by metathesis are monolefins or polyolefins that are linear or cyclic and that carry functional groups, such as, for example, halogens, ethers, nitriles, amines, amides, silanes or ester groups, such as methyl oleate. The process can also use in co-metathesis a mixture of the olefins above.

The metathesis process according to the invention pertains more particularly to rebalancing between one another of the light olefins that are obtained from steam cracking or catalytic cracking (FCC), such as ethylene, propylene, butenes, or pentenes. It makes it possible, for example, to produce propylene from ethylene and a butene-2-rich olefinic $C_4$ fraction, such as a steam-cracking raffinate-2 that was previously subjected to isomerization after removal or transformation of butadiene and isobutene. It is also possible to produce propylene in two stages from a feedstock that contains butene-1 and butene-2 that provides in a first stage propylene and pentene-2, whereby the latter is brought into contact in a second stage with ethylene to provide again propylene as well as butene-1. It also makes it possible to produce a mixture of propylene, isobutene, and butene-1-rich n-butenes from ethylene and a $C_5$ fraction that is enriched with pentene-2 and methyl-2 butene-2. It also makes it possible to produce a mixture of isobutene and butene-1-rich n-butenes from propylene and a $C_5$ fraction that is enriched with pentene-2 and methyl-2 butene-2.

The process according to the invention can be used with a catalyst that is placed in a fixed bed, a fluid bed or a stirred bed, a fluidized bed. The catalyst is advantageously prepared ex-situ and therefore introduced in prepared form into the reactor. The process can be carried out in batch mode, continuously or discontinuously, for example when the flow of the catalyst in a fluid bed is interrupted for a stage of the process.

The process can also be implemented by reactive distillation, whereby the catalytic reaction and the distillation of the reagents and products take place simultaneously in the column.

The reactive distillation column that is used in the process according to the invention can be of any type. In a preferred arrangement, at least one zone that contains the catalyst is arranged. The mechanical arrangement of the catalyst in the catalytic zone or zones is to be such that it impedes the flow of vapor and liquid as little as possible between the two separation zones that enclose it. At the same time, the catalyst is to be used so that an adequate surface area is exposed to catalyze the metathesis reaction suitably. The catalyst can be, for example, used in bulk or in a thin layer on the perforated plates or on grids or in bags that are suspended or placed on substrates that ensure their mechanical behavior or any other way that is known to one skilled in the art. On the other hand, the catalyst can be used in the column to be traversed only by a rising flow of liquid phase. It can also be used in the form of catalytic packing, according to the various known implementations (such as structured packing). The separation zones that enclose the catalytic zones can comprise plates or packing. All of the technologies that are derived from the latter are included here.

As an example of columns, those that are described in documents EP-A-0 332 525, FR-A-2 628 737, FR-A-2 684 893, U.S. Pat. No. 5,221,441 and EP-466 954 will be cited.

The reactive distillation column is operated under such conditions as occur both in the metathesis reaction and a fractionation between the various olefins. For example, the pressure in the column will be adjusted based on the boiling points of the reagents and products, and the optimal temperature of use of the catalyst. The operative temperature can vary from −20 to 200° C., preferably 10 to 100° C., and the pressure can vary from 0.01 to 10 MPa, preferably 0.1 to 5 MPa.

These conditions can also be used on other types of reactors to carry out the metathesis.

According to the invention, the stabilizing agent is injected directly (separately) into the reactor, or into the feedstock that is entering the reactor, or more generally into a reagent or a recycling flow that enters the reactor or else with the catalyst in circulation. The injection is carried out continuously or discontinuously according to needs. It takes place for the entire time of the metathesis reaction. In general, 0.01 to 20%, and preferably 0.01 to 5% by weight of stabilizing agent and in particular of aluminum compound $(RO)_q AlR'_r$, counted relative to the flow that enters the reactor, will be introduced into the reaction medium.

As an illustrative example, the process is now described from FIG. 1, for the production of propylene from ethylene and a butene-2-rich olefinic fraction $C_4$ in an implementation with reactive distillation.

Reactive column (DR) is arranged, for example, with alternate reaction and separation zones. It is supplied by the reagents so that the latter naturally intersect inside due to their respective boiling points. The fresh ethylene (reagent) is thus injected via pipe (1) into the bottom of reactive column (DR) while the feedstock that contains the butene-2-rich olefinic $C_4$ fraction is introduced into the recycling flow (pipe (9) that comes into the high zone of the column) via pipe (2). The stabilizing agent is introduced via a pipe (7) into pipe (9) and is thus injected with the feedstock.

At the top of reactive column (DR), an ethylene-propylene mixture exits via pipe (6). This mixture is separated in distillation column (C1) from where a flow of ethylene that is sent to the bottom of column (DR) after mixing with the fresh ethylene of pipe (1) exits at the top via pipe (5). A small purge for ensuring the elimination of the traces of ethane that are still present in the ethylene is carried out by pipe (4). The propylene that is produced is evacuated via pipe (3) to the bottom of column (C1).

At the bottom of reactive column (DR), a section $C_4^+$ that comprises all of the saturated and olefinic $C_4$ that have not reacted, the $C_5$ and $C_6$ by-product olefins and the stabilizing agent exits via pipe (10).

A small auxiliary column (C2) that is supplied by pipe (10) separates at the top a purge $C_4$ that prevents the accumulation of isobutane and isobutene via pipe (8) and at the bottom a recycling flow $C_4$ via pipe (9). This flow that contains butenes is recycled to column (DR). A purge of the stabilizing agent, of which in general at least one portion is degraded and should be replaced, n-butane and $C_5$ and $C_6$ by-product olefins is ensured via pipe (11).

Figure 2:
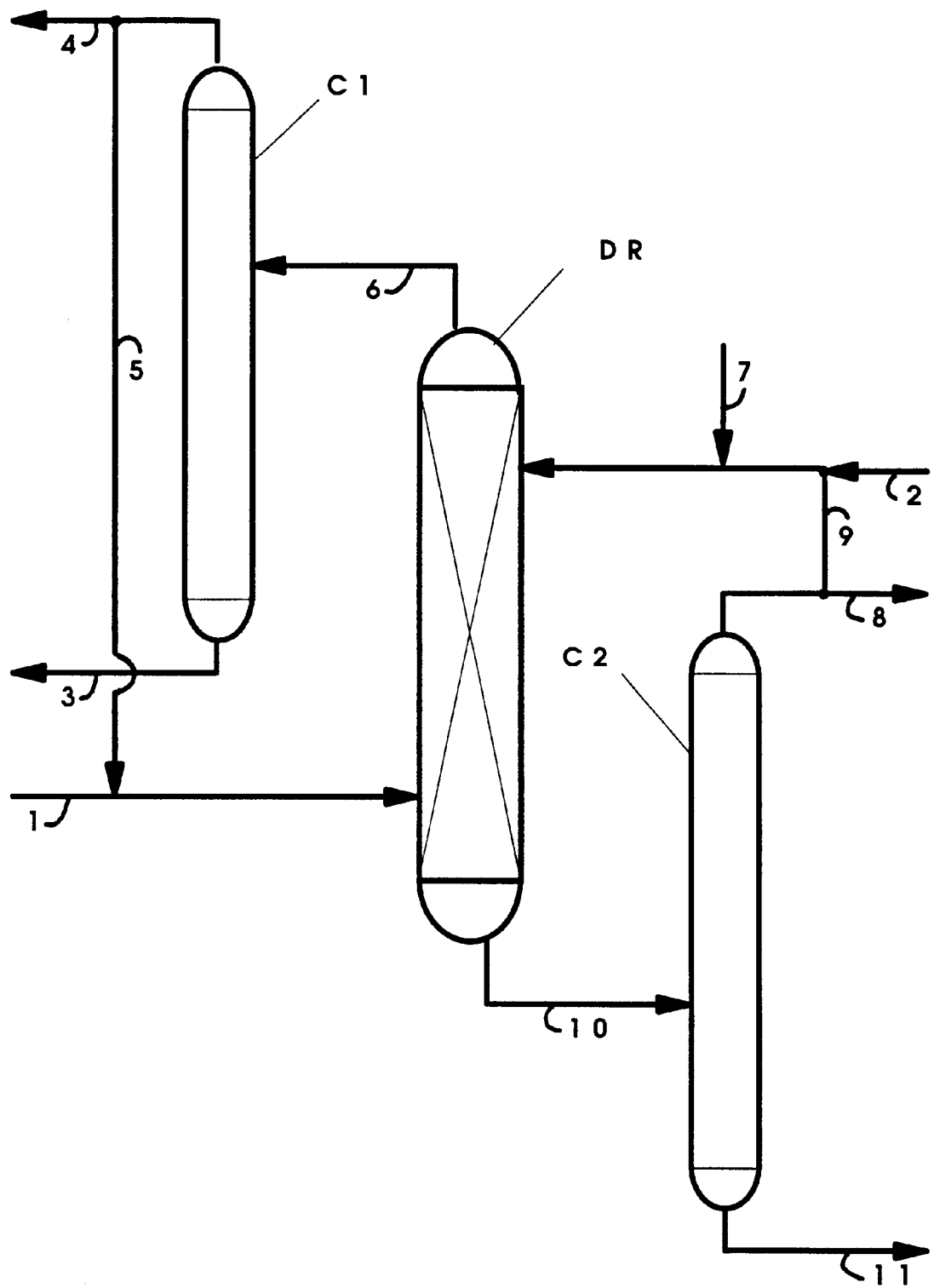

In a variant of this diagram, illustrated by FIG. 2, it is possible to not recycle the stabilizing agent. The $C_4$ recycling flow that is ensured by pipe (9) is then taken on pipe (8) at the top of column (C2), whose operation is to be adapted to this situation. This recycling flow can also be ensured by a lateral draw-off in column (C2). Pipe (11) at the bottom of column (C2) ensures no more than a purge function of the stabilizing agent, n-butane and $C_5$ and $C_6$ by-product olefins. The function of pipe (8) is unchanged, just like the remainder of the diagram.

The following examples illustrate the invention without limiting its scope.

EXAMPLE 1

(Comparative)

Preparation of the Catalyst

In a first stage, a cubic gamma alumina that has a specific surface area of 184 m$^2$/g and a pore volume of 0.67 ml/g is calcined at 300° C. under air. After cooling to ambient temperature, 10 g of calcined alumina is sampled. A solution for the impregnation of rhenium is prepared by diluting 0.24 ml of a concentrated aqueous solution of perrhenic acid that contains 54% by weight of rhenium (specific mass: 2.4 g/ml) in 5 ml of water. This solution is impregnated on the 10 g of alumina that is sampled. After 30 minutes of contact at ambient temperature, the solid that is obtained is dried in a drying oven at 120° C. for one night. It is calcined then dried under a stream of air (about 20 l/h) by passage through a molecular sieve bed at a temperature of 550° C. for 2 hours. During the subsequent cooling period, a stream of dry nitrogen is substituted for the stream of air. The solid that is obtained is maintained and manipulated in dry nitrogen atmosphere. Its metal rhenium content is 3% by weight.

In a 250 ml flask that is placed under argon atmosphere and equipped with a bar magnet, a solution of 0.493 g of triisobutylaluminum in 20 ml of pentane is introduced, and then a solution of 1.095 g of d-t-butyl-2,6-methyl-4-phenol in 30 ml of pentane is injected drop by drop while being stirred and at room temperature. After about 30 hours of reaction, the pentane is evaporated under a vacuum, and the analysis of the remaining white solid indicates that it consists essentially of bis-(di-t-butyl-2,6-methyl-4-phenoxy)-isobutylaluminum. This compound is put back into solution in 5 ml of heptane.

The solution in the heptane of bis-(di-t-butyl-2,6-methyl-4-phenoxy)-isobutylaluminum is then impregnated on the solid that contains the rhenium that is obtained in the first stage. After about 30 minutes of contact, the heptane that is absorbed into the solid is eliminated by evaporation under a vacuum at ambient temperature. A metathesis catalyst that contains 3% by weight of rhenium and 0.67% by weight of aluminum (in addition to the aluminum that is included in the alumina), which is kept in a dry and inert atmosphere before use, is thus obtained.

Use of the Propylene in Metathesis

Examples 1 and 2 relate to the metathesis of propylene for providing ethylene and butene-2. This reaction that is easy to use since it requires only a single reagent is the opposite of the reaction that is described in Example 3 that produces propylene from ethylene and butene-2. The deactivation of the catalyst is the same in these two reactions.

In a reactor that consists of a stainless steel tube that is equipped with a double jacket with water circulation that makes possible the regulation of the temperature, the catalyst that is prepared above is loaded into the fixed bed that is protected from air and moisture. Liquid propylene is injected using a pump through the bottom of the reactor, with a flow rate of 49.6 g/h. The temperature is adjusted to 35° C., and the pressure is kept at 3.5 MPa using a regulator that is placed downstream from the reactor. Under these conditions, the conversion of the propylene at the outlet of the reactor is initially 30% into an equimolar mixture of ethylene and butene-2. It evolves over time as indicated in Table 1. The catalyst lost half of its activity at the end of 30 hours.

EXAMPLE 2

Preparation of the Catalyst

A second feedstock of 10 g of catalyst is prepared according to the operating procedure that is described in Example 1.

Use of the Propylene in Metathesis

The same reactor and the same procedures as in Example 1 are used. Unlike Example 1, however, the metathesis feedstock consists of liquid propylene that is mixed with 0.24% by weight of bis-(di-t-butyl-2,6-methyl-4-phenoxy)-isobutylaluminum. The bis-(di-t-butyl-2,6-methyl-4-phenoxy)-isobutylaluminum was prepared as described in Example 1. The metathesis feedstock is injected using a pump through the bottom of the reactor, with a flow rate of 49.6 g/h. The temperature is adjusted to 35° C., and the pressure is kept at 3.5 MPa. Under these conditions, the conversion of the propylene at the outlet of the reactor is initially 30% of an equimolar mixture of ethylene and butene-2. It evolves over time as indicated in Table 1. The catalyst lost only 16% of its activity at the end of 30 hours.

TABLE 1

| | Conversion of propylene (%) | |
|---|---|---|
| Time (h) | Example 1 | Example 2 |
| 0 | 30 | 30 |
| 10 | 25.8 | 28.9 |
| 20 | 20.3 | 27.4 |
| 30 | 14.6 | 25.6 |

This example illustrates the beneficial effect that is provided by continuous injection with the feedstock of bis-(di-t-butyl-4-phenoxy)-isobutylaluminum.

EXAMPLE 3

The metathesis reaction is carried out in a reactive distillation column. The column consists of a stainless steel drum that has an inside diameter of 5 cm and a height of 250 cm, filled with three packing beds or, in order starting from the bottom: a distillation packing bed over a height of 100 cm, a catalytic packing bed over 50 cm and a distillation packing bed over 100 cm. Each bed is supported by a V-shaped grid, made integral with the drum.

The distillation packing is an unstructured packing that consists of metal elements that have the appearance of approximately helicoidal springs with contiguous coils, a length of 3 mm and a diameter of 1 mm, known under the name of Dixon, and known to be efficient in distillation.

The catalytic packing consists of the distillation packing that is defined above and catalyst that is prepared according to the operating procedure that is described in Example 1. The catalytic packing is obtained by mixing these two components, at a ratio of one volume of catalyst in the form of balls of a mean diameter that is equal to 2 mm, and 25 distillation packing volumes. This mixture is stirred by hand in a glass container to make the distribution of the catalyst homogeneous in the distillation packing.

The column is connected at the bottom to a boiler that is heated electrically and at the top to a condenser and a reflux flask. It is made adiabatic by compensation of heat losses, using ten heating elements that are arranged over its entire height. Each heating element is controlled separately so that the temperature in the immediate vicinity of the outside wall of the column is equal to the one that is established inside the column, on the same side. Further, the column is equipped with sensors and instruments that are necessary for the regulation of the operating parameters.

The column that is thus equipped is operated continuously under a pressure of 2 MPa. It is supplied at the catalytic packing at a rate of 265 g/h by an olefinic fraction that consists primarily of butene-2 (77.3% by weight) and butane, in which bis-(di-t-butyl-2,6-methyl-4-phenoxy)-isobutylaluminum is dissolved at a rate of 0.24% by weight. Bis-(di-t-butyl-2,6-methyl-4-phenoxy)-isobutylaluminum was prepared as described in Example 1. At low catalytic packing, the column receives ethylene with a flow rate of 670 g/h. The heating of the column is regulated so as to separate ethylene and propylene at the top. The reflux rate is set at 1.8.

Under these conditions, after steady operation of the column is achieved, on the one hand 870 g/h of distillate that consists primarily of propylene that has formed (34.4% by weight) and ethylene that has not reacted, and on the other hand 61 g/h of residue that consists of the butane that has remained inert in the reaction and the stabilizing agent are collected.

The distillate that is collected and redistilled according to a known procedure would ultimately provide 300 g/h of propylene and 570 g/h of ethylene which would be for recycling in the reactive distillation column.

What is claimed is:

1. A process comprising performing metathesis of a reaction medium containing olefins in the presence of a catalyst and a stabilizing agent, which reduces deactivation of the catalyst, that is injected into the reaction medium wherein the stabilizing agent is an aluminum compound of the formula I, and wherein the catalyst comprises 0.01%–10% by weight of aluminum in the form of a promoter aluminum compound of the formula II:

$$X_q AlR'_r \qquad \text{I}$$

$$(RO)_q AlR'_r \qquad \text{II}$$

wherein

X is independently RO—, RS—, or $R_2N$— wherein

R is a hydrocarbyl radical of 1 to 40 carbon atoms provided that R is aryl when X is RO—

R' is an alkyl radical of 1 to 20 carbon atoms q is an integer of 1 or 2 r is an integer of 1 or 2 q+r is 3.

2. A process according to claim 1, wherein the stabilizing agent corresponds to formula $(RO)_q AlR'_r$ wherein R is a hydrocarbyl radical that is alkyl, cycloalkyl, alkenyl, aryl, substituted aryl, cycloalkyl a mono to perhalo substituted or mono to peralkoxy substituted or unsubstituted hydrocarbyl radical of 1 to 40 carbon atoms, and R' is a methyl, ethyl, or isobutyl radical, whereby the radicals contain 1 to 20 carbon atoms and whereby the radicals contain 1 to 6 carbon atoms.

3. A process according to claim 1, wherein the stabilizing agent is a compound of the following formula $(RO)_q AlR'_r$ wherein R is a hydrocarbyl radical that is a substituted or unsubstituted aryl radical.

4. A process according to claim 1, wherein the stabilizing agent is bis-(di-t-butyl-2,6-methyl-4-phenoxy)-isobutylaluminum, bis-(di-t-butyl-2,6-methyl-4-phenoxy)-ethyl-aluminum, or bis-(di-t-butyl-2,6-methyl-4-phenoxy)-methyl-aluminum.

5. A process according to claim 1, wherein the process is carried out with a fixed-bed catalyst.

6. A process-according to claim 1, wherein the process is carried out with a fluid-bed or stirred-bed catalyst.

7. A process according to claim 1, wherein the process is carried out with a fluidized-bed catalyst.

8. A process according to claim 1, wherein the process is carried out in a reactive distillation column.

9. A process according to claim 8, wherein the stabilizing agent of the catalyst is injected directly into the reactive distillation column.

10. A process according to claim 1, wherein the process is carried out in a reactive distillation column, in which the catalyst is placed so as to be traversed only by a rising flow of liquid phase.

11. A process according to claim 1, wherein the stabilizing agent of the catalyst is mixed with the olefinic feedstock.

12. A process according to claim 1, wherein the catalyst comprises a porous mineral substrate, 0.01 to 20% by weight of rhenium in oxide form, and 0.01 to 10% by weight of aluminum that is introduced in the form of a promoter aluminum compound of formula II of claim 1, $(RO)_q AlR'_r$.

13. A process according to claim 1, wherein a feedstock that consists of ethylene and a butene-2-rich $C_4$ fraction is brought into contact with the catalyst to produce propylene.

14. A process according to claim 1, wherein a feedstock that consists of ethylene and a $C_5$ fraction that is enriched with pentene-2 and methyl-2-butene-2 is brought into contact with the catalyst to produce propylene, isobutene and n-butenes.

15. A process according to claim 1, wherein a feedstock that consists of propylene and a $C_5$ fraction that is enriched with pentene-2 and methyl-2-butene-2 is brought into contact with the catalyst to produce isobutene and n-butenes.

16. A process according to claim 1, wherein it operates at a temperature of between −20 and 200° C. and under a pressure of 0.01 to 10 MPa.

17. A process according to claim 1, wherein 0.01 to 20% by weight of stabilizing agent (counted relative to the flow that enters the reactor) is added during the reaction.

* * * * *